United States Patent [19]

Kajiyama et al.

[11] 4,279,158
[45] Jul. 21, 1981

[54] ULTRASONIC FLAW DETECTOR DRIVING APPARATUS

[75] Inventors: Sigeru Kajiyama; Kimio Kanda, both of Hitachi; Sakae Sugiyama, Ibaraki, all of Japan

[73] Assignees: Hitachi, Ltd.; Babcock-Hitachi Kabushiki Kaisha, both of Tokyo, Japan

[21] Appl. No.: 61,050

[22] Filed: Jul. 26, 1979

[30] Foreign Application Priority Data

Jul. 28, 1978 [JP] Japan .................................. 53-92939

[51] Int. Cl.³ .......................................... G01N 29/04
[52] U.S. Cl. ..................................................... 73/637
[58] Field of Search ........................ 73/618, 620–621, 73/622, 633, 635, 637

[56] References Cited

U.S. PATENT DOCUMENTS 3,921,440  11/1975  Toth ....................... 73/622

Primary Examiner—James J. Gill
Attorney, Agent, or Firm—Craig and Antonelli

[57] ABSTRACT

A ultrasonic flaw detector driving apparatus including a driving apparatus which is equipped with an arm mounted respective side faces of a main frame of the ultrasonic flaw detector driving apparatus so as to allow the arms to move into an open and closed position. A resilient member provides a force which acts on the respective arms in such a direction so as to urge the arms into the open position. A ratchet prevents the arms from being opened by the resilient member as teeth engage with a pawl in a stepwise manner. Rollers are rotatably mounted to a tip of the respective arms and are in rolling contact with the guide rail on which the driving apparatus travels. The arms are moved to the open for mounting the driving apparatus to the guide rail and thereafter the arms are moved to the closed position. Thus, the main frame of the driving apparatus can be position movably fixed onto the guide rail.

10 Claims, 4 Drawing Figures

U.S. Patent   Jul. 21, 1981   Sheet 2 of 2   4,279,158
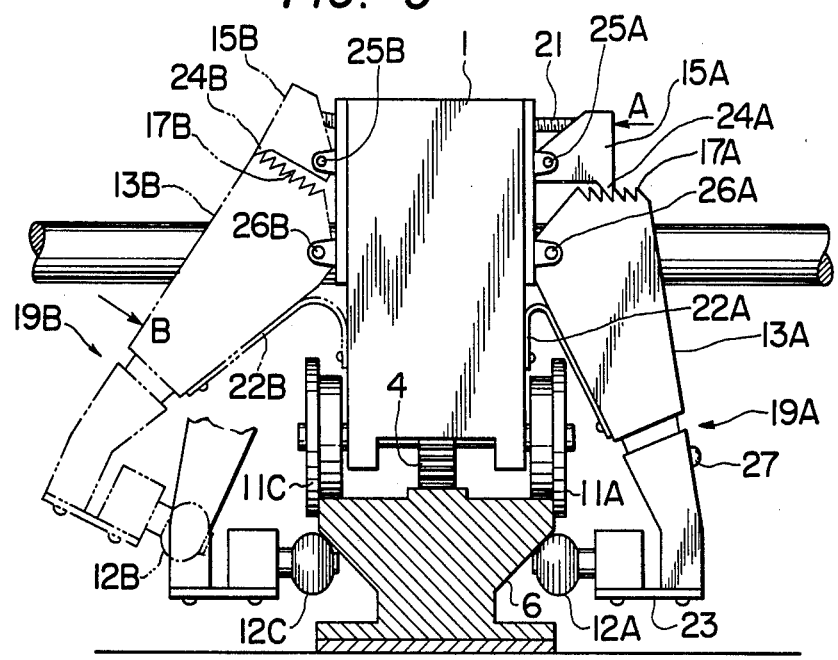
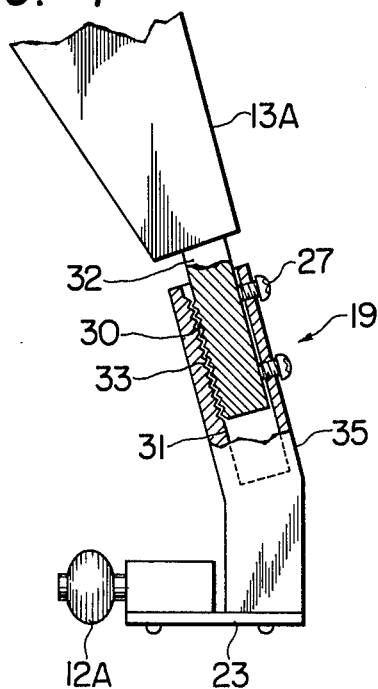

ULTRASONIC FLAW DETECTOR DRIVING APPARATUS

BACKGROUND OF THE INVENTION

This invention relates to a ultrasonic flaw detector driving apparatus for a pressure container, pipings, etc. of an atomic power plant. More specifically, the present invention relates to a mounting-dismounting mechanism of a remote-controlled, automatic ultrasonic flaw detector driving apparatus.

Regulations require the periodic inspection of a pressure container and a piping arrangement of an atomic power plant and also a nozzle portion as the joint portion of these members. For example, in the United States of America, the contents of this inspection is stipulated in detail in ASME (THE AMERICAL SOCIETY OF MECHANICAL ENGINEERS) CODE.

The inspection is generally carried out by fitting a guide rail around an object for inspection such as the pressure container or the piping and mounting a ultrasonic flaw detector driving apparatus having a ultrasonic wave probe onto the guide rail and causing it to travel thereon. Since the inspection procedure consists principally of the manual work, there are problems such as exposure of an inspector to the radioactive rays and difference in the collected data depending upon inspectors. Hence, there is a pressing need for a reliable remote-control ultrasonic flaw detector driving apparatus. However, there are strict conditions imposed on a ultrasonic flaw detector driving apparatus to be installed on the site of the inspection with regard to the functional requirements such as, scanning accuracy, weight, size, mounting-dismounting time as well as the performance aspects such as flaw detection accuracy. To this date, no apparatus has been developed which perfectly satisfies all these requirements.

As to the problem of the weight of the driving apparatus, for example, the ultrasonic flaw detector driving apparatus must be light enough for the inspector to carry it around to and from necessary positions of the object for inspection because he has sometimes to climb up and down a ladder or to pass through a narrow and limited foothold between pipings while taking the driving apparatus with him. Moreover, the fitting height and length of the driving apparatus are limited depending upon the structure of the pipings around it when the former is mounted to the latter. Though this limitation is not determined primarily, it is preferred to reduce the size of the driving apparatus to widen the range of its application. In order to minimize the exposure of the inspector to the radioactive rays, it is also necessary to reduce the time required for fitting the driving apparatus to the guide rail as short as possible. For these reasons, it is desired to obtain such a mounting-dismounting mechanism of one-touch system that is capable of shortening the time required for mounting and dismounting the ultrasonic flaw detector driving apparatus.

Further, since the site of the inspection work is of a multi-storied construction, any dropping of tools, would lead to a great danger. Hence, no tool is preferably used for mounting and dismounting the driving apparatus. In addition, the driving apparatus must be able to scan the probe up to a desired position of the object for inspection with a high level of accuracy and must have such versatility so as to be adapted to pipings of a varying diameter by simply replacing the guide rail.

SUMMARY OF THE INVENTION

The present invention is therefore directed to providing an ultrasonic flaw detector driving apparatus which can easily be mounted to a guide rail fitted around a pressure container, pipings or the like.

It is another object of the present invention to provide a ultrasonic flaw detector driving apparatus which is small in size but has versatility for various objects for inspection.

The present invention uses a ratchet in combination with a spring as a mechanism for performing the mounting and dismounting work of the driving apparatus to and from the guide rail. Accordingly, when the driving apparatus is mounted and clamped to the guide rail, the driving apparatus is allowed to limitedly move only in a direction to hold the guide rail by engaging a pawl with teeth moving unidirectionally. When the driving apparatus is to be dismounted from the guide rail, a guide rail holding mechanism is caused to open its legs by a spring through a simple onetouch operation to float and disengage the pawl.

BRIEF DESCRIPTION OF THE DRAWING

FIG. 3 is a schematic view useful for explaining the construction and action of the ultrasonic flaw detector driving apparatus in accordance with the present invention; and FIG. 4 is a schematic view of a holding mechanism of the ultrasonic flaw detector driving apparatus in accordance with the present invention.

DESCRIPTION OF THE PREFERRED EMBODIMENTS

Before explaining the embodiments of the present invention, explanation will first be made of the conventional technique by referring to FIG. 1.

Figure 1:
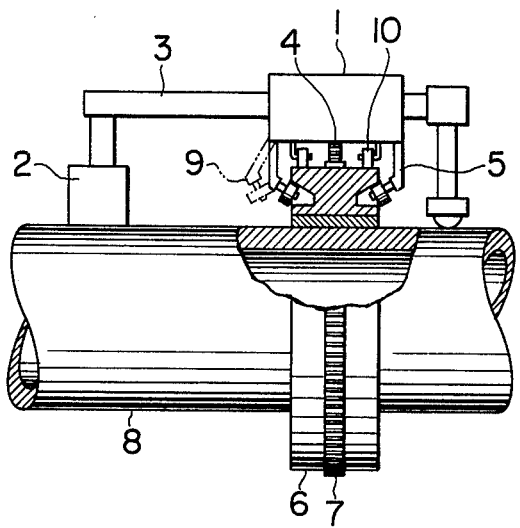
FIG. 1 is a schematic view of a conventional ultrasonic flaw detector driving apparatus fitted to guide rail arranged on a piping.

FIG. 1 shows the conventional ultrasonic flaw detector driving apparatus, mounted to the guide rail, that is arranged around the piping of the atomic power plant, wherein reference numeral 1 represents the main frame of the driving apparatus and a probe 2 is shown fitted to the main frame 1 by means of an arm 3. The main frame 1 of the driving apparatus is mounted to the guide rail 6 by means of a holding mechanism 5. Though the holding mechanism 5 is shown fitted to the guide rail 6 with its legs being closed, the legs may be opened as in the holding mechanism 9 which is indicated in phantom line. In other words, the holding mechanism is mounted to, and detached from, the guide rail 6 while its legs are being closed and opened.

The main frame 1 of the driving apparatus mounted to the guide rail in this manner incorporates therein a motor which turns a pinion 4 to engage with a rack 7 on the guide rail 6 so that the main frame 1 is allowed to scan an object 8 for inspection in a circumferential direction. The main frame 1 incorporates therein another motor which moves the probe-holding arm 3 in the axial direction to thereby scan the probe 2 in the axial direction.

As one of the conventional methods of fitting the main frame 1 of the driving apparatus to the guide rail, there is a method which secures the holding mechanism 5 to the main frame 1 using a screw or an air piston while it holds the guide rail 6 (in the state of the holding mechanism 5 as illustrated in FIG. 1).

However, the problem with using a screw is that it is necessary to use a tool and the fitting time becomes long. While the method of using an air piston is not free from the problems with such a method the mechanism becomes inevitably complicated and large and a piping arrangement of the air becomes necessary because the driving source such as an air pressure must be used.

On the other hand, a pair of rollers 10, which together with the holding mechanism travels on the guide rail 6, must be disposed inside the driving apparatus 1 so that the height of the driving apparatus becomes higher.

When a piping is the object for inspection and when the diameter of the piping varies, the gap between the roller of the holding mechanism 5 and the roller 10 also varies correspondingly. In the conventional holding mechanism, therefore, the roller gap must be changed every time the diameter of the piping varies.

Next, the embodiments of the present invention will be explained in detail by referring to FIGS. 2 et seq.

Figure 2:
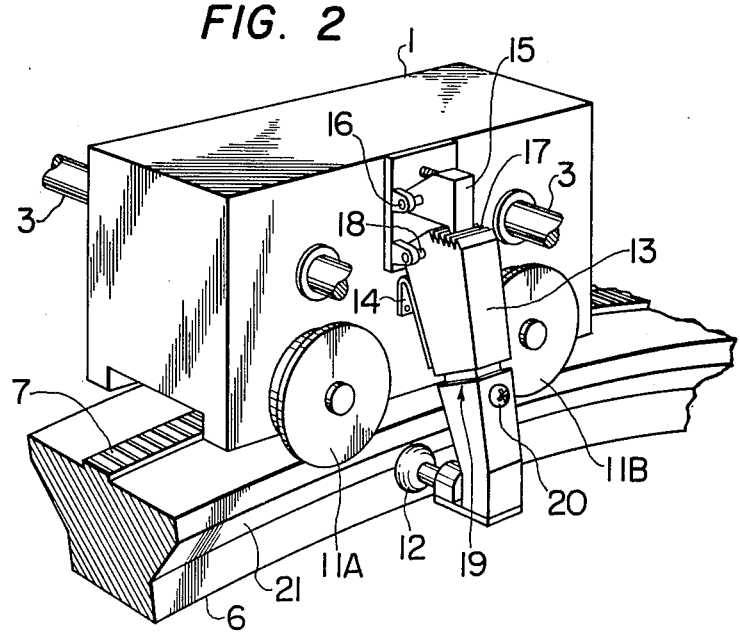
FIG. 2 is a perspective view of principal portions of the ultrasonic flaw detector driving apparatus in accordance with the present invention.

FIG. 2 shows a part of the remote automatic ultrasonic flaw detector driving apparatus, especially its mounting mechanism to a guide rail 6. The main frame 1 of the driving apparatus is fitted to the guide rail 6 that is in turn fitted to a piping or the like. The driving apparatus turns the pinion 4 (FIG. 3) fitted coaxially with the roller 11A by means of the motor incorporated therein and thus travels on the rack 7 fitted onto the guide rail 6. At the same time, a probe (not shown), fitted to the main frame 1, is also caused to turn in the circumferential direction. The main frame 1 also incorporates another motor which moves the probe-holding arm 3 in the axial direction, thereby allowing the probe to scan in the axial direction.

The driving apparatus 1 is mounted to the guide rail 6 so as to support the latter by means of the rollers 11A, 11B mounted to the side faces of the driving apparatus 1. The rollers 11A, 11B travel on the upper face of the guide rail 6 and by a roller 12, pushed onto a slope portion 21 of the guide rail 6 so as to come into rolling contact with the sloped portion 21. The holding mechanism is disposed on each side of the driving apparatus 1 and has such a construction that, when the arm 13 is pushed in the direction of the guide rail 6, the roller 12, disposed at the tip of the arm 13, moves with a shaft 18 being as its center.

Teeth 17 are formed at the other end of the arm 13 while a pawl is formed at the tip of lever 15 so that they mutually receive a reaction force of a spring 14. Accordingly, during mounting of the drivinfg apparatus 1 to the guide rail 6, the arm 13 is allowed to slide only unidirectionally. Dismounting of the driving apparatus 1 from the guide rail 6 can be accomplished by simply pushing the lever 15 up towards the driving apparatus 1 while the arm 13 is pushed towards the driving apparatus 1. When the lever 15 is pushed up, the pawl at the tip of the lever 15 is disengaged from the teeth 17 whereby the legs of the arm 13 are opened by the force of the spring 14 and the roller 12 is thereby detached from the slope portion 21 of the guide rail 6.

Next, the principle of action of the apparatus in accordance with the present invention will be explained in detail with reference to FIG. 3.

FIG. 3 is a side view of FIG. 2 and the holding mechanism indicated by the solid line on the right hand side of FIG. 3 illustrates the state in which the driving apparatus 1 is mounted to the guide rail 6, with the phantom line illustration of the holding mechanism on the lefthand side of FIG. 3 illustrating the state in which the driving apparatus 1 is dismounted from the guide rail. The driving apparatus 1 can be mounted to the guide rail 6 by pushing the rollers 11A, 11C and the arm 13 to the slope portion of the guide rail 6 in a direction designated by the reference character B so as to put the roller 12A at the tip of the guide rail 6. The roller 12C on the opposite side can also be fitted in the same way. When the driving apparatus 1 travels on the guide rail 6, the rollers 12A and 12C turn and run simultaneously with the rollers 11A and 11C.

On the other hand, it is possible to keep the angle of the arm 13A constant by causing a pawl 24A at a tip of a lever 15A to engage with teeth 17A of a ratchet provided at the other end of the arm 13A. In this instance, the pawl 24A at the tip of the lever 15A is pushed by the spring 21 in the direction for engagement with the teeth 17A with the shaft 25A being as its center. When the arm 13A is pushed, the roller 12A rotates with the shaft 26A being as its base and the pawl 24A moves on the teeth 17A one after another. In this case, the arm 13A moves, while being limited, in the direction to push the guide rail 6. When a force is caused to act on the pawl 14A by means of the spring 21 to engage with the teeth 17A, another force is simultaneously caused to act by means of the spring 22A on the arm 13A in a direction so as to allow the teeth 17A to engage with the pawl 24A. When the teeth 17A are large, the roller 12A moves stepwise so that there could be a case where a constant pushing force to the guide rail 6 cannot be obtained. For this reason, it is necessary to reduce the pitch of the teeth 17A and to use a spring 23 so as to absorb discontinuity arising from the pitch of the teeth 17A. If the reaction force of the spring 23 is weak, however, the holding force relative to the guide rail 6 becomes weak. Hence, the spring 23 must have a considerable force of reaction.

For dismounting the driving apparatus 1 from the guide rail 6, a force is manually applied to the lever 15A in the direction indicated by the arrow A. The lever 15A rotates in direction so as to compress the spring 21 with the shaft 25A being as its center so that the pawl 24A is disengaged from the teeth 17A and the arm 13A opens its legs by means of the force of reaction of the spring 22A with the shaft 26A being as its center. Thus, the roller 12A is disengaged from the guide rail 6. The positions assumed by the elements of the holding mechanism in the dismounted condition are illustrated in phantom lines on the lefthand side of FIG. 3 with the reference numerals for the corresponding elements in the righthand side of the figure being followed by the reference character B.

From the state shown in FIG. 2, the diameter of the guide rail 6 varies in accordance with the diameter of the piping. Hence, it is necessary to be able to vary the relative position between the rollers mounted on the side faces of the drive apparatus 1 and the rollers 12A, 12B. For this purpose, it is effective to provide the arm 13 with a retraction mechanism, to be described more fully hereinbelow in connection with FIG. 4, to allow it to slide in accordance with the change in the curvature of the guide rail 6. A lock screw 20 (FIG. 2) maybe used for mixing a length of the arm 13 in accordance with a desired curvature of the guide rail 6.

As shown in FIG. 4 the retraction mechanism generally designated by the reference numeral 19 of the arm 13A includes a retractile arm 35 having an opening 31. A shaft 32, an integral structure of the arm 13A, is inserted into the opening 31. Grooves 30 and 33 are formed on one side of the shaft 32 and on the open side of the retractile arm 35 opposing to said one side so as to engage with each other. The position of the roller 12A can be selected optionally by changing the position of engagement between the shaft 32 and the opening 31. The retractile arm 35 is interconnected to the arm 13A by a lock screw 27 at a position adapted to the guide rail.

In order for the driving apparatus to accurately travel along the guide rail 6, it is effective to provide steps to the rollers 11A and 11C so as to clamp the corner of the guide rail 6 as shown in FIG. 3, instead of simply placing them onto the guide rail 6.

Though the above-described embodiment uses one holding roller 12A or 12C on each side or a total of two rollers, the number of the rollers is not particularly limitative. For example, it is possible to align two rollers on each side in the circumferential direction of the guide rail so as to provide for a total of four rollers.

Methods of extension and retraction of the retractile arm and its fixing method are not limitative, either.

If the pitch of the teeth 17A is made small, a rigid body, rather than the spring 23 in FIG. 3 may be used without any problem.

In the embodiment described, the slope portion is formed on the guide rail 6 and is brought into contact with the holding rollers 12A, 12B. This arrangement is not limitative, either. The slope portion may be eliminated from the guide rail 6 if a curvature or an inclination is given to the outer face of the roller. If the roller can be fixed in accordance with quantity of its movement, it does not depart from the object of the present invention.

The springs 22A and 23 shown in FIG. 3 need not necessarily be a leaf spring and a coiled spring, respectively, and other resilient materials may also be used.

Though the arm 13 shown in FIG. 2 is of the type which holds the guide rail 6 from both sides, it is not particularly limited to such a type. For example, while its one side is kept stationary, the arm 13 may hold the guide rail 6 only from its other side.

Moreover, though the arm 13 is shown arranged at right angles to the guide rail in FIG. 2, this angle is by no means limitative. For example, the arm 13 may be disposed at an angle approximately parallel to the guide rail 6.

What is claimed is:

1. An ultrasonic flaw detector driving apparatus movable on a guide rail for enabling a detecting of a flaw of an object for inspection, the ultrasonic flaw detector driving apparatus includes a main frame, characterized in that means are provided for movably holding the main frame of said driving apparatus on said guide rail including
    at least one arm mounted on at least one side face of said main frame of said driving apparatus in such a manner so as to allow the arm to move in an opening and a closing direction, teeth formed at one end of said arm, a pawl mounted on said driving apparatus, said pawl being adapted to be brought into engagment with and to be disengaged from said teeth, first resilient means for providing a force acting on the at least one arm in such direction so as to cause said teeth to be engaged by said pawl, and roller means mounted on said at least one arm, the roller means being adapted to be brought into rolling contact with said guide rail, said at least one arm extends in a direction substantially perpendicular to a longitudinal direction of the guide rail when said at least one arm is in a closed position.

2. The ultrasonic flaw detector driving apparatus as defined in claim 1, characterized in that means are provided for changing a length of said at least one arm.

3. The ultrasonic flaw detector driving apparatus as defined in one of claims 1 or 2, characterized in that second resilient means are provided for mounting said roller means on said at least one arm.

4. The ultrasonic flaw detector driving apparatus as defined in claim 3 characterized in that said first resilient means includes a first spring for imparting a force on said at least one arm in the opening direction, and a second spring for imparting a force on the pawl in an engaging direction with said teeth.

5. The ultrasonic flaw detector driving apparatus as defined in claim 1 or 2, characterized in that said first resilient means includes a first spring for imparting a force on said at least one arm in the opening direction, and a second spring for imparting a force on the pawl in an engaging direction with said teeth.

6. The ultrasonic flaw detector driving apparatus as defined in one of claims 1 or 2, characterized in that at least one further arm is mounted on a second side face of the main frame in such a manner so as to allow the further arm to move in an opening and closing direction, teeth are formed at one end of the further arm, a further pawl is mounted on said driving apparatus, said further pawl being adapted to be brought into engagement with the teeth formed on the further arm, a further resilient means is provided for imparting a force on the further arm acting in a direction so as to cause said teeth on said further arm to be engaged by said further pawl, and in that roller means are mounted on said further arm and are adapted to be brought into rolling contact with the guide rail.

7. The ultrasonic flaw detector driving apparatus as defined in claim 6, characterized in that means are provided for changing a length of each of said arms.

8. The ultrasonic flaw detector driving apparatus as defined in claim 7, characterized in that resilient means are provided for mounting the roller means on the respective arms.

9. The ultrasonic flaw detector driving apparatus as defined in claim 8, characterized in that the first resilient means and further resilient means each include a first spring for imparting a force on the respective arms in the opening direction, and a second spring for imparting a force on the respective pawls in an engaging direction with said teeth.

10. The ultrasonic flaw detector driving apparatus as defined in claim 9, characterized in that the means for changing a length of each of said arms includes a shaft portion to be formed on the respective arms, a retractable arm portion having an opening for accommodating the shaft portion, and means formed on the shaft portion and retractable arm portion for engagement with each other so as to maintain the respective arms at selective lengths.

* * * * *